United States Patent [19]

Miner et al.

[11] Patent Number: 4,470,976

[45] Date of Patent: Sep. 11, 1984

[54] POLY-CATION SALT OF 4-O-POLYHEXAOSE-THIO-ARYLENE SULFATES

[75] Inventors: Thomas G. Miner, Sugarloaf, N.Y.; Robert E. Schaub, Upper Saddle River, N.J.; Seymour Bernstein, New City, N.Y.

[73] Assignee: American Cyanamid Company, Stamford, Conn.

[21] Appl. No.: 527,528

[22] Filed: Aug. 29, 1983

[51] Int. Cl.³ .................. A61K 31/70; C07H 15/20
[52] U.S. Cl. .................................. 424/180; 536/4.1; 536/17.2; 536/17.5; 536/17.6; 536/17.8; 536/17.9; 536/118; 536/121; 536/122; 536/18.1

[58] Field of Search .............. 424/180; 536/118, 122, 536/17.2, 17.5, 17.6, 17.9, 4.1, 17.8, 121

[56] References Cited

U.S. PATENT DOCUMENTS 4,399,126  8/1983  Schaub et al. ..................... 536/118
4,407,796 10/1983  Miner et al. ........................ 536/118

*Primary Examiner*—Johnnie R. Brown
*Attorney, Agent, or Firm*—A. M. Rosenblum

[57] ABSTRACT

Poly-cation salts of 4-O-polyhexaose-thio-arylene sulfate derivatives, useful as modulators of the complement system, the intermediates thereof and the process of making such intermediates and products.

19 Claims, No Drawings

POLY-CATION SALT OF 4-O-POLYHEXAOSE-THIO-ARYLENE SULFATES

BACKGROUND OF THE INVENTION

1. Field of the Invention

The present invention relates to novel cation salts of 4-O-polyhexaose-thio-arylene sulfate derivatives, to their use as modulators of the complement system of warm-blooded animals, to the intermediates thereof and to the process for the preparation of such intermediates and products.

2. Description of the Prior Art

The term "complement" refers to a complex group of proteins in body fluids that, working together with antibodies or other factors, play an important role as mediators of immune, allergic, immunochemical and/or immunopathological reactions. The reactions in which complement participates take place in blood serum or in other body fluids, and hence are considered to be humoral reactions.

With regard to human blood, there are at present more than 20 proteins in the complement system consisting of the so-called classical and alternative pathways. These complement proteins are generally designated by the letter C and by number: C1, C2, C3 and so on up to C9. The complement protein C1 is actually an assembly of subunits designated C1q, C1r and C1s. The numbers assigned to the complement proteins reflect the sequence in which they become active, with the exception of complement protein C4, which reacts after C1 and before C2. The numerical assignments for the proteins in the complement system were made before the reaction sequence was fully understood. A more detailed discussion of the complement system and its biochemical, biological and pathological role in the body processes can be found in, for example, Bull. W. H. O. 39: 935 (1968); Annu. Rev. Med. 19: 1 (1968); Johns Hopkins Med. J. 128: 57 (1971); Harvey Lect. 66: 75 (1972); N. Engl. J. Med. 287: 452, 489, 545, 592, 642 (1972); Sci. Am. 229 (5): 54 (1973); Fed. Pro. 32: 134 (1973); Med. World, Oct. 11, 1974, p. 53; J. Allergy Clin. Immunol. 53: 298 (1974); Cold Spring Harbor Conf. Cell Proliferation 2/Proteases Biol. Control: 229 (1975); Annu. Rev. Biochem. 44: 697 (1975); Complement in Clinical Medicine, Dis. Mon. (1975); Complement, Scope, December 1975; Ann. Intern. Med. 84: 580 (1976); Transplant. Rev.: 32 (1976); "Complement: Mechanisms and Functions," Prentice-Hall, Englewood Cliffs, N.J. (1976); Essays Med. Biochem. 2: 1 (1976); Hosp. Pract. 12: 33 (1977); Perturbation of Complement in Disease, Chap. 15 in Biol. Amplification Systems in Immunol. (Ed. Day and Good), Plenum, New York and London (1977); Am. J. Clin. Pathol. 68: 647 (1977); Biochem. Soc. Trans. 5: 1959 (1977); Harvey Lect. 72: 139 (1976–1977); J. Periodontol. 48: 505 (1977); Biochem. Soc. Trans. 6: 798 (1978); Clin. and Exp. Dermatol. 4: 271 (1979); Infect. Dis. Rev. 1: 483 (1979).

The complement system (e.g., classical pathway) can be considered to consist of three subsystems: (1) a recognition unit (C1q) which enables it to combine with antibody molecules that have detected a foreign invader; (2) an activation unit (C1r, C1s, C2, C4, C3) which prepares a site on the neighboring membrane; and (3) an attack unit (C5, C6, C7, C8 and C9) which creates a "hole" in the membrane. The membrane attack unit is nonspecific; it destroys invaders only because it is generated in their neighborhood. In order to minimize damage to the host's own cells, its activity must be limited in time. This limitation is accomplished partly by the spontaneous decay of activated complement and partly by interference by inhibitors and destructive enzymes. The control of complement, however, is not perfect, and there are times when damage is done to host's cells. Immunity is, therefore, a double-edged sword.

Activation of the complement system also accelerates blood clotting. This action comes about by way of the complement-mediated release of a clotting factor from platelets. The biologically active complement fragments and complexes can become involved in reactions that damage the host's cells. These pathogenic reactions can result in the development of immune-complex diseases. For example, in some forms of nephritis, complement damages the basal membrane of the kidney, resulting in the escape of protein from the blood into the urine. The disease disseminated lupus erythematosus belongs in this category; its symptoms include nephritis, visceral lesions and skin eruptions. The treatment of diphtheria or tetanus with the injection of large amounts of antitoxin sometimes results in serum sickness, an immune-complex disease. Rheumatoid arthritis also involves immune complexes. Like disseminated lupus erythematosus, it is an autoimmune disease in which the disease symptoms are caused by pathological effects of the immune system in the host's tissues. In summary, the complement system has been shown to be involved with inflammation, coagulation, fibrinolysis, antibody-antigen reactions and other metabolic processes.

In the presence of antibody-antigen complexes the complement proteins are involved in a series of reactions which may lead to irreversible membrane damage if they occur in the vicinity of biological membranes. Thus, while complement constitutes a part of the body's defense mechanism against infection it also results in inflammation and tissue damage in the immunopathological process. The nature of certain complement proteins, suggestions regarding the mode of complement binding to biological membranes and the manner in which complement effects membrane damage are discussed in Annu. Rev. Biochem. 38: 389 (1969); J. Exp. Med. 141: 724 (1975); J. Immunol. 116: 1431 (1976); 119: 1, 1195, 1358, 1482 (1977); 120: 1841 (1978); Immunochemistry 115: 813 (1978); J. Biol. Chem. 254: 9908 (1979).

A variety of substances have been disclosed as inhibiting the complement system, i.e., as complement inhibitors. For example, the compounds, 3,3'-ureylenebis[6-(2-amino-8-hydroxy-6-sulfo-1-naphthylazo)benzenesulfonic acid], tetrasodium salt (chlorazol fast pink), heparin and a sulphated dextran have been reported to have an anticomplementary effect, Br. J. Exp. Pathol. 33: 327 (1952). German Pat. No. 2,254,893 or South African Pat. No. 727,923 discloses certain 1-(diphenylmethyl)-4-(3-phenylallyl)piperazines useful as complement inhibitors. Other chemical compounds having complement inhibiting activity are disclosed in, for example, J. Med. Chem. 12: 415, 902, 1049, 1053 (1969); Can. J. Biochem. 47: 547 (1969); J. Immunol. 104: 279 (1970); J. Immunol. 106: 241 (1971); J. Immunol. 111: 1061 (1973); Biochim. Biophys. Acta 317: 539 (1973); Life Sci. 13: 351 (1973); J. Immunol. 113: 584 (1974); Immunology 26: 819 (1974); J. Med. Chem. 17: 1160 (1974); Biochem. Biophys. Res. Comm. 67: 225 (1975); Ann. N.Y. Acad. Sci. 256: 441 (1975); J. Med. Chem. 19: 634, 1079 (1976); J. Immunol. 118: 466 (1977); Arch. Int. Pharmacodyn. 226: 281 (1977); Biochem. Pharmacol. 26: 325 (1977); J. Pharm. Sci. 66: 1367 (1977); Chem. Pharm. Bull. 25: 1202 (1977); Biochim. Biophys. Acta 484: 417 (1977); J. Clin. Microbiol. 5: 278 (1977); Immunochemistry 15: 231 (1978); Immunology 34: 509 (1978); J. Exp. Med. 147: 409 (1978); Thromb. Res. 14: 179 (1979); J. Immunol. 122: 2418 (1979); J. Chem. Soc. Chem. Comm. 726 (1979); Immunology 36: 131 (1979); Biochem. Biophys. Acta 611: 196 (1980); and J. Med. Chem. 23: 240 (1980).

It has been reported that the known complement inhibitors, epsilon-aminocaproic acid and tranexamic acid, have been used with success in the treatment of hereditary angioneurotic edema, a disease state resulting from an inherited deficiency or lack of function of the serum inhibitor of the activated first component of complement (C1 inhibitor), N. Engl. J. Med. 286: 808 (1972); 287: 452 (1972); Ann. Intern. Med. 84: 580 (1976); J. Allergy Clin. Immunol. 60: 38 (1977). Also androgenic steroids have been used successfully in the treatment of this physiological disorder; see Medicine 58: 321 (1979); Arthritis Rheum. 22: 1295 (1979); Am. J. Med. 66: 681 (1979); and J. Allergy Clin. Immunol. 65: 75 (1980).

It has also been reported that the drug pentosanpolysulfoester has an anticomplementary activity on human serum, both in vitro and in vivo, as judged by the reduction in total hemolytic complement activity, Pathol. Biol. 25: 33; 25 (2): 105; 25 (3): 179 (1977).

SUMMARY OF THE INVENTION

This invention relates to new compounds which are 4-O-polyhexaose-thio-arylene sulfate derivatives and the cation salts thereof, that modulate the complement system, thereby modulating complement activity in body fluids. Moreover, this invention involves a method of modulating the complement system in a body fluid which comprises subjecting body fluid complement to the action of an effective complement modulating amount of the above-identified compounds. This invention further concerns a method of modulating the complement system in a warm-blooded animal which comprises administering to said animal an effective complement modulating amount of the above-identified compounds.

This invention also deals with the novel precursors that act as intermediates in preparing the above-described complement modulating compounds.

DETAILED DESCRIPTION OF THE INVENTION

In accordance with the present invention, there are provided novel compounds represented by the following generic formula I:

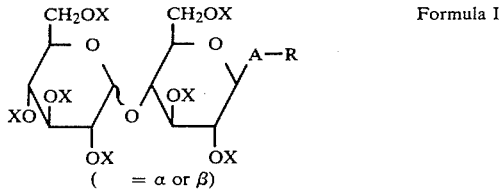

wherein X is —SO$_3$M and M is a nontoxic pharmaceutically acceptable cation salt, wherein the salt forming moiety is selected from the group consisting of alkali metal, alkaline earth metal, aluminum, ammonia, zinc and substituted ammonia selected from the group consisting of trialkylamine (C$_1$–C$_6$), piperidine, pyrazine, alkanolamine (C$_2$–C$_6$) and cycloalkylamine (C$_3$–C$_6$); A is selected from the group consisting of —S— and —SO—; and R is phenyl mono-, di- or trisubstituted with a moiety selected from the group consisting of hydrogen, OX, alkoxy (C$_1$–C$_3$), hydroxy, halo, trifluoromethyl, amino, mercapto, acetylamino, —COOM, —NHCOCOOC$_2$H$_5$ and

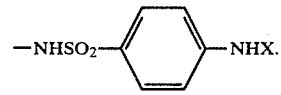

Particularly preferred compounds of Formula I which are of major interest as modulators of the complement system include the following:

2,5-bis(sulfooxy)phenyl 2,3,6-tri-O-sulfo-4-O-(2,3,4,6-tetra-O-sulfo-α-D-glucopyranosyl)-1-thio-β-D-glucopyranoside nonasodium salt 2,5-bis(sulfooxy)phenyl 2,3,6-tri-O-sulfo-4-O-(2,3,4,6-tetra-O-sulfo-α-D-glucopyranosyl)-1-thio-β-D-glucopyranoside nonatriethylammonium salt 4-(sulfanilamido)phenyl 2,3,6-tri-O-sulfo-4-O-(2,3,4,6-tetra-O-sulfo-α-D-glucopyranosyl)-1-thio-β-D-glucopyranoside octasodium salt 4-(sulfanilamido)phenyl 2,3,6-tri-O-sulfo-4-O-(2,3,4,6-tetra-O-sulfo-α-D-glucopyranosyl)-1-thio-β-D-glucopyranoside octatriethylammonium salt 2,5-bis(sulfooxy)phenyl 2,3,6-tri-O-sulfo-4-O-(2,3,4,6-tetra-O-sulfo-α-D-glucopyranosyl)-1-sulfinyl-β-D-glucopyranoside nonasodium salt 2,5-bis(sulfooxy)phenyl 2,3,6-tri-O-sulfo-4-O-(2,3,4,6-tetra-O-sulfo-α-D-glucopyranosyl)-1-sulfinyl-β-D-glucopyranoside nonatriethylammonium salt 4-methoxyphenyl 2,3,6-tri-O-sulfo-4-O-(2,3,4,6-tetra-O-sulfo-α-D-glucopyranosyl)-1-thio-62-D-glucopyranoside heptasodium salt 4-methoxyphenyl 2,3,6-tri-O-sulfo-4-O-(2,3,4,6-tetra-O-sulfo-α-D-glucopyranosyl)-1-thio-β-D-glucopyranoside heptatriethylammonium salt 4-aminophenyl 2,3,6-tri-O-sulfo-4-O-(2,3,4,6-tetra-O-sulfo-α-D-glucopyranosyl)-1-thio-β-D-glucopyranoside heptasodium salt 4-aminophenyl 2,3,6-tri-O-sulfo-4-O-(2,3,4,6-tetra-O-sulfo-α-D-glucopyranosyl)-1-thio-β-D-glucopyranoside heptatriethylammonium salt 4-aminophenyl 2,3,6-tri-O-sulfo-4-O-(2,3,4,6-tetra-O-sulfo-β-D-glucopyranosyl)-1-thio-β-D-glucopyranoside heptasodium salt 4-aminophenyl 2,3,6-tri-O-sulfo-4-O-(2,3,4,6-tetra-O-sulfo-β-D-glucopyranosyl)-1-thio-β-D-glucopyranoside heptatriethylammonium salt 4-(sulfooxy)phenyl 2,3,6-tri-O-sulfo-4-O-(2,3,4,6-tetra-O-sulfo-α-D-glucopyranosyl)-1-thio-β-D-glucopyranoside octasodium salt 4-(sulfooxy)phenyl 2,3,6-tri-O-sulfo-4-O-(2,3,4,6-tetra-O-sulfo-α-D-glucopyranosyl)-1-thio-β-D-glucopyranoside octatriethylammonium salt 2-carboxyphenyl 2,3,6-tri-O-sulfo-4-O-(2,3,4,6-tetra-O-sulfo-α-D-glucopyranosyl)-1-thio-β-D-glucopyranoside octasodium salt 2-carboxyphenyl 2,3,6-tri-O-sulfo-4-O-(2,3,4,6-tetra-O-sulfo-α-D-glucopyranosyl)-1-thio-β-D-glucopyranoside octatriethylammonium salt 4-fluorophenyl 2,3,6-tri-O-sulfo-4-O-(2,3,4,6-tetra-O-sulfo-α-D-glucopyranosyl)-1-thio-β-D-glucopyranoside heptasodium salt 4-fluorophenyl 2,3,6-tri-O-sulfo-4-O-(2,3,4,6-tetra-O-sulfo-α-D-glucopyranosyl)-1-thio-β-D-glucopyranoside heptatriethylammonium salt 3-trifluoromethylphenyl 2,3,6-tri-O-sulfo-4-O-(2,3,4,6-tetra-O-sulfo-α-D-glucopyranosyl)-1-thio-β-D-glucopyranoside heptasodium salt 3-trifluoromethylphenyl 2,3,6-tri-O-sulfo-4-O-(2,3,4,6-tetra-O-sulfo-α-D-glucopyranosyl)-1-thio-β-D-glucopyranoside heptatriethylammonium salt 4-(ethoxyoxalylamino)phenyl 2,3,6-tri-O-sulfo-4-O-(2,3,4,6-tetra-O-sulfo-α-D-glucopyranosyl)-1-thio-β-D-glucopyranoside heptasodium salt 4-(ethoxyoxalylamino)phenyl 2,3,6-tri-O-sulfo-4-O-(2,3,4,6-tetra-O-sulfo-α-D-glucopyranosyl)-1-thio-β-D-glucopyranoside heptatriethylammonium salt 3-mercaptophenyl 2,3,6-tri-O-sulfo-4-O-(2,3,4,6-tetra-O-sulfo-α-D-glucopyranosyl)-1-thio-β-D-glucopyranoside octasodium salt 3-mercaptophenyl 2,3,6-tri-O-sulfo-4-O-(2,3,4,6-tetra-O-sulfo-α-D-glucopyranosyl)-1-thio-β-D-glucopyranoside octratriethylammonium salt 4-acetamidophenyl 2,3,6-tri-O-sulfo-4-O-(2,3,4,6-tetra-O-sulfo-β-D-glucopyranosyl)-1-thio-β-D-glucopyranoside heptasodium salt 4-acetamidophenyl 2,3,6-tri-O-sulfo-4-O-(2,3,4,6-tetra-O-sulfo-β-D-glucopyranosyl)-1-thio-β-D-glucopyranoside heptatriethylammonium salt 4-acetamidophenyl 2,3,6-tri-O-sulfo-4-O-(2,3,4,6-tetra-O-sulfo-α-D-glucopyranosyl)-1-thio-β-D-glucopyranoside heptasodium salt 4-acetamidophenyl 2,3,6-tri-O-sulfo-4-O-(2,3,4,6-tetra-O-sulfo-α-D-glucopyranosyl)-1-thio-β-D-glucopyranoside heptatriethylammonium salt.

Although the compounds of Formula I are shown as being fully sulfated, this invention contemplates partially sulfated products. This invention further contemplates other sugars such as aldo- or keto-hexoses or pentoses or uronic acids.

This invention further deals with a method of modulating the complement system in a body fluid, such as blood serum, which comprises subjecting body fluid complement to the action of an effective complement modulating amount of a compound of the above formula I. Body fluids can include blood, plasma, serum, synovial fluid, cerebrospinal fluid, or pathological accumulations of fluid such as pleural effusion, etc. This invention also concerns a method of modulating the complement system in a warmblooded animal which comprises administering to said animal an effective complement modulating amount of a compound of the above formula I.

In addition, this invention is concerned with the precursors in the preparation of the complement modulating compounds of formula I, shown by the following formula II:

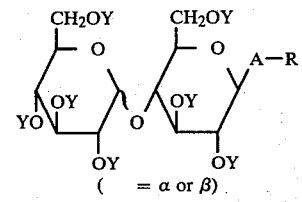

Formula II wherein Y is selected from the group consisting of hydrogen and —COCH₃, and A and R are as described in formula I.

Specific compounds of formula II which are of particular interest as intermediates for the production of the compounds of formula I include the following:

2,5-dihydroxyphenyl 2,3,6-tri-O-acetyl-4-O-(2,3,4,6-tetra-O-acetyl-α-D-glucopyranosyl)-1-thio-β-D-glucopyranoside 4-(N-acetylsulfanilamidophenyl) 2,3,6-tri-O-acetyl-4-O-(2,3,4,6-tetra-O-acetylα-D-glucopyranosyl)-1-thio-β-D-glucopyranoside 4-methoxyphenyl 2,3,6-tri-O-acetyl-4-O-(2,3,4,6-tetra-O-acetyl-α-D-glucopyranosyl)-1-thio-β-D-glucopyranoside 4-aminophenyl 2,3,6-tri-O-acetyl-4-O-(2,3,4,6-tetra-O-acetyl-α-D-glucopyranosyl)-1-thio-β-D-glucopyranoside 4-hydroxyphenyl 2,3,6-tri-O-acetyl-4-O-(2,3,4,6-tetra-O-acetyl-α-D-glucopyranosyl)-1-thio-β-D-glucopyranoside 2-carboxyphenyl 2,3,6-tri-O-acetyl-4-O-(2,3,4,6-tetra-O-acetyl-β-D-glucopyranosyl)-1-thio-β-D-glucopyranoside 4-fluorophenyl 2,3,6-tri-O-acetyl-4-O-(2,3,4,6-tetra-O-acetyl-α-D-glucopyranosyl)-1-thio-β-D-glucopyranoside 3-trifluoromethylphenyl 2,3,6-tri-O-acetyl-4-O-(2,3,4,6-tetra-O-acetyl-α-D-glucopyranosyl)-1-thio-β-D-glucopyranoside 4-(ethoxyoxalylamino)phenyl 2,3,6-tri-O-acetyl-4-O-(2,3,4,6-tetra-O-acetyl-α-D-glucopyranosyl)-1-thio-β-D-glucopyranoside 3-mercaptophenyl 2,3,6-tri-O-acetyl-4-O-(2,3,4,6-tetra-O-acetyl-α-D-glucopyranosyl)-1-thio-β-D-glucopyranoside 2,5-dihydroxyphenyl 2,3,6-tri-O-acetyl-4-O-(2,3,4,6-tetra-O-acetyl-α-D-glucopyranosyl)-1-sulfinyl-β-D-glucopyranoside 4-aminophenyl 2,3,6-tri-O-acetyl-4-O-(2,3,4,6-tetra-O-acetyl-β-D-glucopyranosyl)-1-thio-β-D-glucopyranoside 2,5-dihydroxyphenyl 4-O-(α-D-glucopyranosyl)-1-thio-β-D-glucopyranoside 4-(sulfanilamido)phenyl 4-O-(α-D-glucopyranosyl)-1-thio-β-D-glucopyranoside 4-methoxyphenyl 4-O-(α-D-glucopyranosyl)-1-thio-β-D-glucopyranoside 4-aminophenyl 4-O-(α-D-glucopyranosyl)-1-thio-β-D-glucopyranoside 4-hydroxyphenyl 4-O-(α-D-glucopyranosyl)-1-thio-β-D-glucopyranoside 2-carboxyphenyl 4-O-(α-D-glucopyranosyl)-1-thio-β-D-glucopyranoside 4-fluorophenyl 4-O-(α-D-glucopyranosyl)-1-thio-β-D-glucopyranoside 3-trifluoromethylphenyl 4-O-(α-D-glucopyranosyl)-1-thio-β-D-glucopyranoside 4-(ethoxyoxalylamino)phenyl 4-O-(α-D-glucopyranosyl)-1-thio-β-D-glucopyranoside 3-mercaptophenyl 4-O-(α-D-glucopyranosyl)-1-thio-β-D-glucopyranoside 4-acetamidophenyl 4-O-(α-D-glucopyranosyl)-1-thio-β-D-glucopyranoside 2,5-dihydroxyphenyl 4-O-(α-D-glucopyranosyl)-1-sulfinyl-β-D-glucopyranoside 4-aminophenyl 4-O-(β-D-glucopyranosyl)-1-thio-β-D-glucopyranoside 4-acetamidophenyl 4-O-(β-D-glucopyranosyl)-1-thio-β-D-glucopyranoside.

In the above formulas I and II the sugar molecule is drawn to represent either maltose or cellobiose. This invention is not restricted to these two disaccharides, but instead is intended to include disaccharides consisting of aldohexoses, ketohexoses, aldopentoses and the like.

The compounds of formula I find utility as complement modulators in body fluids and as such may be used to ameliorate or prevent those pathological reactions requiring the function of complement and in the therapeutic treatment of warm-blooded animals having immunologic diseases such as rheumatoid arthritis, systemic lupus erythematosus, certain kinds of glomerulonephritis, certain kinds of autoallergic hemolytic anemia, certain kinds of platelet disorders and certain kinds of vasculitis. These compounds may also be used in the therapeutic treatment of warm-blooded animals having nonimmunologic diseases such as paroxysmal nocturnal hemoglobinurea, hereditary angioneurotic edema and inflammatory states induced by the action of bacterial or lysosomal enzymes on the appropriate complement components as, for example, inflammation following coronary occlusion. They also may be useful in the treatment of transplant rejection and ulcers and as blood culture and transport mediums. The sulfated compounds of this invention such as the sodium and aluminum salts, may be particularly useful in the treatment of ulcers and the like on oral therapy. Also, the non-sulfated intermediate compounds of formula II may be useful as immuno-enhancing agents or potentiators.

The compounds of this invention may be prepared according to the following flowchart.

FLOWCHART

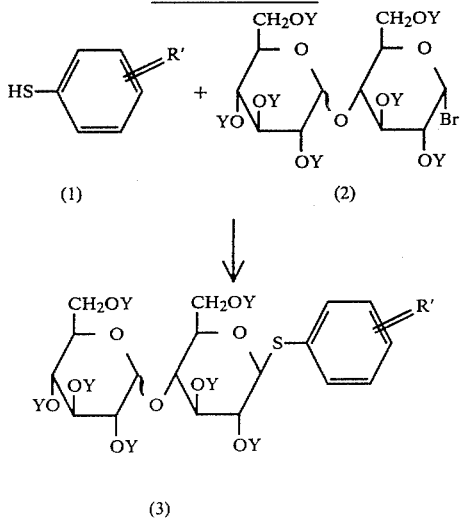

(1)  (2)

(3)

-continued
FLOWCHART

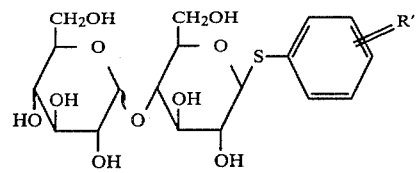

(4)

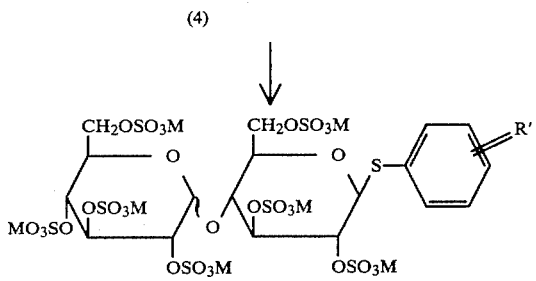

(5)

In accordance with the above flowchart, a mono-, di- or trisubstituted thiophenol (1) is reacted with an α-acetobromodisaccharide (2) and sodium hydride in tetrahydrofuran at reflux for several hours and then purified by chromatography, giving a substituted arylene polyacetyl disaccharide (3), where Y is —COCH$_3$ and R' represents the phenyl substituents listed above, which is then reacted with a solution of 2N triethylamine:methanol:water (3:6:2) at −5° to +25° C., followed by refrigeration for 16–40 hours, giving a substituted arylene disaccharide (4) which is then reacted with triethylamine-sulfur trioxide complex in dry N,N-dimethylacetamide at 65° C. for 5–10 hours followed by extraction with acetone giving the compounds (5), where M is NH(C$_1$–C$_6$ alkyl)$_3$$^+$, which is then converted to the salt (5) where M is as described above.

It is generally preferred that the respective product of each process step, described hereinabove, is separated and/or isolated prior to its use as starting material for subsequent steps. Separation and isolation can be effected by any suitable purification procedure such as, for example, evaporation, crystallization, column chromatography, distillation, etc. Also it should be appreciated that when typical reaction conditions (e.g., temperatures, mole ratios, reaction times) have been given, the conditions which are both above and below these specified ranges can also be used, though generally less conveniently.

The term "pharmaceutically acceptable salt" refers to those salts of the parent compound which do not significantly or adversely affect the pharmaceutical properties (e.g., toxicity, effectiveness, etc.) of the parent compound. The salt forming moiety of the present invention which is pharmaceutically acceptable includes the alkali metals (e.g., sodium, potassium, etc.); alkaline earth metals (e.g., calcium, etc.); aluminum; zinc; ammonia; and substituted ammonia selected from the group consisting of trialkylamine (C$_1$–C$_6$), piperidine, pyrazine, alkanolamine (C$_2$–C$_6$) and cycloalkylamine (C$_3$–C$_6$).

The term "trialkylamine ($C_1$–$C_6$)" defines those amines having three aliphatic fully saturated hydrocarbon substituents containing 1 to 6 carbon atoms either linearly or branched. Typically, these amines are trimethylamine, triethylamine, tripropylamine, dimethylethylamine, dimethyl-1-propylamine, etc. The term "alkanolamine ($C_2$–$C_6$)" refers to the above-defined trialkylamines additionally substituted with at least one and not more than three hydroxy groups on at least two of the alkyl hydrocarbon chains. Such amines are, for example, triethanolamine, tripropanolamine, etc. The term "cycloalkylamine ($C_3$–$C_6$)" is defined as the 3 to 6 fully saturated carbocyclic moieties such as cyclopropyl, methylcyclobutyl, cyclopentyl, cyclohexyl, etc.

As used hereinabove and below unless expressly stated to the contrary, all temperatures and temperature ranges refer to the centigrade system and the terms "ambient" or "room temperature" refer to about 25° C. The term "percent" or "(%)" refers to weight percent and the terms "mole" and "moles" refer to gram moles. The term "equivalent" refers to a quantity of reagent equal in moles to the moles of the preceding or succeeding reactant recited in the Preparation or Example in the term of moles of finite weight or volume.

Whereas the exact scope of the instant invention is set forth in the appended claims, the following specific examples illustrate certain aspects of the present invention. However, the examples are set forth for illustration only and are not to be construed as limitations on the present invention except as set forth in the appended claims.

A further understanding of the invention can be obtained from the following non-limiting Preparations and Examples.

EXAMPLE 1

2,5-Dihydroxyphenyl 2,3,6-tri-O-acetyl-4-O-(2,3,4,6-tetra-O-acetyl-α-D-glucopyranosyl)-1-thio-β-D-glucopyranoside A slurry of 7.0 g of acetobromomaltose, 4.5 g of thiourea, 1.52 g of potassium carbonate and 5 ml of acetone was heated at reflux for 15 minutes, then cooled and the solid collected. This solid was dissolved in 25 ml of water containing 1.5 g of potassium carbonate, stirred for ½ hour, then neutralized to pH 4 and extracted with dichloromethane. The organic extract was dried, concentrated in vacuo to a white powder and then chromatographed on silica gel using the system 97% dichloromethane-3% ethanol, giving from fractions 1–3, 3.6 g of solid which was rechromatographed (40% ethyl acetate in hexane) giving 1.9 g of 2,3,6-tri-O-acetyl-4-O-(2,3,4,6-tetra-O-acetyl-α-D-glucopyranosyl)-1-thio-β-D-glucopyranoside.

A mixture of 1.6 g of the above material, 0.3 g of benzoquinone, 50 ml of dry tetrahydrofuran and 250 mg of sodium acetate were combined under argon and stirred overnight. The reaction was then diluted with 50 ml of water and extracted with three 100 ml portions of ethyl acetate. The organic extracts were combined, washed with 25 ml of water, dried and concentrated in vacuo to a tarry liquid. This liquid was purified by chromatography, giving 1.3 g of the desired intermediate as a yellow liquid, $[\alpha]_D^{26} = -18° \pm 2°$ (0.549% chloroform).

EXAMPLE 2

2,5-Dihydroxyphenyl 4-O-(α-D-glucopyranosyl)-1-thio-β-D-glucopyranoside

To a solution of 14.0 g of 2,5-dihydroxyphenyl 2,3,6-tri-O-acetyl-4-O-(2,3,4,6-tetra-O-acetyl-α-D-glucopyranosyl)-1-thio-β-D-glucopyranoside in 100 ml of absolute methanol under argon at 5° C. was added 0.6 g of sodium spheres in oil. The reaction was stirred at room temperature for one hour, then 20 ml of a strongly acidic sulfonic acid cation exchanger, for example, Dowex ® 50WX8 ($H^+$) resin (Dow), was added, the mixture was stirred 10 minutes then filtered and concentrated in vacuo, giving 9.19 g of the desired intermediate as a dark brown solid, $[\alpha]_D^{26} = +52° \pm 2°$ (0.51% methanol).

EXAMPLE 3

2,5-Bis(sulfooxy)phenyl 2,3,6-tri-O-sulfo-4-O-(2,3,4,6-tetra-O-sulfo-α-D-glucopyranosyl)-1-thio-β-D-glucopyranoside nonasodium salt A solution of 0.8 g of 2,5-dihydroxyphenyl 4-O-(α-D-glucopyranosyl)-1-thio-β-D-glucopyranoside and 4.3 g of triethylamine-sulfur trioxide complex in 10 ml of dry N,N-dimethylacetamide was heated under argon at 80° C. overnight, then cooled and poured into 200 ml of 2-methyl-3-pentanone containing 20 ml of diatomaceous earth. The pad was washed with 20 ml of acetone and extracted with 50 ml of water. The aqueous extract was neutralized to pH 7 with 15 ml of a weakly acidic carboxylic acid cation exchanger, for example, Bio Rex ® 70 ($Na^+$) resin (Biorad), and then lyophilized, giving 3 g of the nonatriethylamine derivative as a solid. This solid was dissolved in 20 ml of water containing one gram of sodium acetate, then diluted with 200 ml of ethanol. The resulting solid was collected, giving 2.1 g of the desired nonasodium salt as a tan solid, $[\alpha]_D^{26} = +17° \pm 1°$ (1.18%, water).

EXAMPLE 4

2,5-Dihydroxyphenyl 2,3,6-tri-O-acetyl-4-O-(2,3,4,6-tetra-O-acetyl-α-D-glucopyranosyl)-1-sulfinyl-β-D-glucopyranoside A solution of 5.0 g of p-benzoquinone in 25 ml of dimethoxyethane was added to a stirred mixture of 29.8 g of 2,3,6-tri-O-acetyl-4-O-(2,3,4,6-tetra-O-acetyl-α-D-glucopyranosyl)-1-thio-β-D-glucopyranoside and 2.8 g of acetic acid in 25 ml of dimethoxyethane. After 2 hours of stirring the solution was concentrated in vacuo, giving 33.3 g of reddish solid. This solid was purified by chromatography, giving 5.54 g of the desired intermediate as a yellow solid $[\alpha]_D^{26} = +54° \pm 1°$ (0.941%, methanol).

EXAMPLE 5

2,5-Dihydroxyphenyl 4-O-(α-D-glucopyranosyl)-1-sulfinyl-β-D-glucopyranoside

A 3.5 g portion of 2,5-dihydroxyphenyl 2,3,6-tri-O-acetyl-4-O-(2,3,4,6-tetra-O-acetyl-α-D-glucopyranosyl)-1-sulfinyl-β-D-glucopyranoside was reacted as described in Example 2, giving 2.07 g of the desired intermediate as a light brown solid, $[\alpha]_D^{26} = +67° \pm 2°$ (0.525%, dimethylsulfoxide).

EXAMPLE 6

2,5-Bis(sulfooxy)phenyl 2,3,6-tri-O-sulfo-4-O-(2,3,4,6-tetra-O-sulfo-α-D-glucopyranosyl)-1-sulfinyl-β-D-glucopyranoside nonasodium salt A solution of 1.82 g of 2,5-dihydroxyphenyl 4-O-(α-D-glucopyranosyl)-1-sulfinyl-β-D-glucopyranoside and 18.4 g of triethylamine-sulfur trioxide complex in 20 ml of N,N-dimethylacetamide was stirred over 1.1 g of 4 Å molecular sieves at 65° C. for 5 hours. The reaction was cooled, diluted with one ml of triethylamine and poured into 500 ml of acetone. The occluding liquid (which contains the nonatriethylammonium derivative) was dissolved in 20 ml of water containing 5.6 g of sodium acetate, stirred for ½ hour and filtered into 500 ml of ethanol. The mixture was chilled and the resulting solid collected, giving 4.07 g of the desired nonasodium salt as a tan solid, $[\alpha]_D^{26} = +21° \pm 1°$ (1.064%, water).

EXAMPLE 7

4-Methoxyphenyl 2,3,6-tri-O-acetyl-4-O-(2,3,4,6-tetra-O-acetyl-α-D-glucopyranosyl)-1-thio-β-D-glucopyranoside To a slurry of 0.6 g of hexane washed, 50% sodium hydride in oil in 40 ml of dry tetrahydrofuran was added a solution of 1.68 g of 4-methoxythiophenol in 10 ml of dry tetrahydrofuran. After stirring ½ hour, a solution of 7.0 g of α-acetobromomaltose in 50 ml of dry tetrahydrofuran was added. This mixture was stirred overnight and then refluxed for 16 hours. The mixture was then extracted with 25 ml of 1N sodium hydroxide followed by 25 ml of water. The organic layer was dried, evaporated to a solid and purified by chromatography, giving 3.2 g of the desired intermediate as a white solid, mp 72°–74° C.

EXAMPLE 8

4-Methoxyphenyl 4-O-(α-D-glucopyranosyl)-1-thio-β-D-glucopyranoside

A mixture comprising 2.6 g of 4-methoxyphenyl 2,3,6-tri-O-acetyl-4-O-(2,3,4,6-tetra-O-acetyl-α-D-glucopyranosyl)-1-thio-β-D-glucopyranoside in 25 ml of cold methanol was combined with a cold mixture of 2N triethylamine in methanol:water (6:2). This mixture was refrigerated overnight, then evaporated in vacuo to a solid which was triturated with ether, giving 1.3 g of the desired intermediate, UV 225–245 nm.

EXAMPLE 9

4-Methoxyphenyl 2,3,6-tri-O-sulfo-4-O-(2,3,4,6-tetra-O-sulfo-α-D-glucopyranosyl)-1-thio-β-D-glucopyranoside heptasodium salt A mixture of 1.3 g of 4-methoxyphenyl 4-O-(α-D-glucopyranosyl)-1-thio-β-D-glucopyranoside and 5.3 g of triethylamine-sulfur trioxide complex in 50 ml of dry acetone over one gram of 4 Å molecular sieves was heated at reflux for 7 hours, then cooled and filtered. The filtrate was concentrated to a solid which is the heptatriethylammonium derivative. This solid was taken up in 25 ml of acetone. The lower phase was reextracted with acetone and then concentrated. The concentrate was preabsorbed on 5 g of polyamide resin and placed on 100 g of polyamide resin. This was eluted with 500 ml of acetone, then by 500 ml of water and finally by 500 ml of 0.01N ammonium hydroxide. The eluates were combined, placed on a Dowex® 50WX8 (Na+) resin column and eluted with water. The eluate was concentrated to a solid which was placed on polyamide resin and washed with 500 ml of water. The eluate was concentrated, giving the desired heptasodium derivative as a white solid, $[\alpha]_D^{26} = +24° \pm 3°$ (0.321%, water).

EXAMPLE 10

2-Carboxyphenyl 2,3,6-tri-O-acetyl-4-O-(2,3,4,6-tetra-O-acetyl-α-D-glucopyranosyl)-1-thio-β-D-glucopyranoside To a slurry of 96 mg of 50% sodium hydride in oil, in 20 ml of dimethoxyethane was added 150 mg of thiosalicyclic acid. After gas evolution subsided, the reaction was chilled to −10° C. under argon and 70 mg of α-acetobromomaltose in 10 ml of dimethoxyethane was added. The reaction was stirred for 72 hours, 2 ml of acetone were added followed by 25 ml of water. The reaction was extracted with ethyl acetate, neutralized and extracted with water, giving 600 mg of the desired intermediate, $[\alpha]_D^{26} = +21°$ (methanol).

EXAMPLE 11

2-Carboxyphenyl 4-O-(α-D-glucopyranosyl)-1-thio-β-D-glucopyranoside

A solution of 1.6 g of 2-carboxyphenyl 2,3,6-tri-O-acetyl-4-O-(2,3,4,6-tetra-O-acetyl-α-D-glucopyranosyl)-1-thio-β-D-glucopyranoside in 15 ml of a mixture of 2N triethylamine:methanol:water (3:6:2) was stirred for 16 hours, then concentrated in vacuo to a solid. This solid was dissolved in water, adjusted to pH 3.5, diluted further with water producing a slurry which was applied to 150 ml of a polystyrene resin, for example, Amberlite® XAD-2 resin (Norman Haase) and then eluted with 500 ml of water followed by one liter of 80% methanol. The methanol eluate give 0.6 g of the desired intermediate as a solid.

EXAMPLE 12

2-Carboxyphenyl 2,3,6-tri-O-sulfo-4-O-(2,3,4,6-tetra-O-sulfo-α-D-glucopyranosyl)-1-thio-β-D-glucopyranoside octasodium salt A mixture of 0.6 g of 2-carboxyphenyl 4-O-(α-D-glucopyranosyl)-1-thio-β-D-glucopyranoside, 1.1 g of 4 Å molecular sieves and 2.72 g of triethylamine-sulfur trioxide complex in 5 ml of dry N,N-dimethylacetamide was heated at 60° C. for 5 hours under argon, then cooled and poured into 200 ml of stirred actone. After ½ hour the mixture was filtered through diatomaceous earth. The tacky solid, which is the octatriethylammonium salt, was dissolved in 5 ml of water containing one gram of sodium acetate and 3 g of Bio Rex® 70 (Na+) resin. The mixture was stirred 15 minutes, then filtered and the filtrate gradually diluted with 200 ml of ethanol and then refrigerated giving 0.7 g of the desired octasodium salt as a tan solid, $[\alpha]_D^{26} = +9° \pm 2°$ (0.918%, water).

EXAMPLE 13

4-Hydroxyphenyl 2,3,6-tri-O-acetyl-4-O-(2,3,4,6-tetra-O-acetyl-α-D-glucopyranosyl)-1-thio-β-D-glucopyranoside To a slurry of 0.48 g of hexane washed sodium hydride in oil in 80 ml of dry dimethoxyethane was added 7.0 g of α-acetobromomaltose and 1.3 g of 4-hydroxythiophenol in 20 ml of dry dimethoxyethane under argon at −5° C. The reaction was allowed to warm to room temperature over 48 hours and was then poured through a bed composed of 20 ml of diatomaceous earth and 10 ml of hydrous magnesium silicate. The bed was eluted with 60 ml of ether then 60 ml of ethyl acetate and finally 60 ml of methanol. The ether extract was extracted with three 50 ml portions of water, then dried and concentrated to a solid. The ethyl acetate extract was also concentrated to a solid. These two solids were combined, dissolved in ethyl acetate and purified by chromatography, giving 4.4 g of the desired intermediate as an oil, $[\alpha]_D^{26} = +38° \pm 2°$ (0.541%, methanol).

EXAMPLE 14

4-Hydroxyphenyl 4-O-(α-D-glucopyranosyl)-1-thio-β-D-glucopyranoside

A solution of 4.0 g of 4-hydroxyphenyl 2,3,6-tri-O-acetyl-4-O-(2,3,4,6-tetra-O-acetyl-α-D-glucopyranosyl)-1-thio-β-D-glucopyranoside in 53 ml of a mixture of 2N triethylamine:methanol:water (3:6:2) was stirred for 4 hours, chilled overnight and then concentrated to an oil. This oil was dissolved in water, extracted with three 500 ml portions of ether and both the water and ether layers were concentrated and combined. The combined concentrate was dissolved in 200 ml of water, acidified to pH 4 and chromatographed on Amberlite ® XAD-2 resin, eluting with 500 ml of water, then 500 ml of methanol. The methanol extract was concentrated, giving 1.2 g of the desired intermediate $[\alpha]_D^{26} = +31° \pm 1°$ (1.144%, methanol).

EXAMPLE 15

4-Sulfooxyphenyl 2,3,6-tri-O-sulfo-4-O-(2,3,4,6-tetra-O-sulfo-α-D-glucopyranosyl)-1-thio-β-D-glucopyranoside octasodium salt A solution of 1.1 g of 4-hydroxyphenyl 4-O-(α-D-glucopyranosyl)-1-thio-β-D-glucopyranoside and 5.3 g of triethylamine-sulfur trioxide complex in 1.0 ml of dimethylacetamide over 1.5 g of 4 Å molecular sieves was stirred under argon at 70° C. for 16 hours. The reaction was then cooled, filtered and diluted to 200 ml with acetone. The phases were separated by pouring through a pad of diatomaceous earth and eluting the pad with 50 ml of water into a flask containing 10.1 g of Bio Rex ® (Na+) ion exchange resin. The resin slurry was stirred 15 minutes, filtered, concentrated and freeze-dried, giving 3.0 g of the octatriethylamine derivative. This solid was dissolved in 10 ml of water containing 1.7 g of sodium acetate, stirred for 15 minutes and poured into 190 ml of isopropanol. The solid was collected, giving 1.8 g of the desired octasodium salt as a tan solid, $[\alpha]_D^{26} = +31° \pm 1°$ (0.949%, water).

EXAMPLE 16

4-Fluorophenyl 2,3,6-tri-O-acetyl-4-O-(2,3,4,6-tetra-O-acetyl-α-D-glucopyranosyl)-1-thio-β-D-glucopyranoside A 1.4 g portion of 4-fluorothiophenol and 7.0 g of α-acetobromomaltose in 50 ml of tetrahydrofuran was added to a slurry of 0.53 g of hexane washed sodium hydride (50% in oil) in 50 ml of tetrahydrofuran, under argon at 5° C. The reaction was stirred for 2 hours at room temperature, then heated at reflux for one hour. After cooling the solution was filtered, concentrated, and purified by chromatography, giving 4.8 g of the intermediate as a white solid, $[\alpha]_D^{26} = +43° \pm 1°$ (0.862%, methanol).

EXAMPLE 17

4-Fluorophenyl 4-O-(α-D-glucopyranosyl)-1-thio-β-D-glucopyranoside

A 4.0 g portion of 4-fluorophenyl 2,3,6-tri-O-acetyl-4-O-(2,3,4,6-tetra-O-acetyl-α-D-glucopyranosyl)-1-thio-β-D-glucopyranoside was reacted as described in Example 8, giving 2.2 g of the intermediate as a white solid, $[\alpha]_D^{26} = +52° \pm 1°$ (0.872%, methanol).

EXAMPLE 18

4-Fluorophenyl 2,3,6-tri-O-sulfo-4-O-(2,3,4,6-tetra-O-sulfo-α-D-glucopyranosyl)-1-thio-β-D-glucopyranoside heptasodium salt A solution of 2.0 g of 4-fluorophenyl 4-O-(α-D-glucopyranosyl)-1-thio-β-D-glucopyranoside and 8.4 g of triethylamine-sulfur trioxide complex in 10 ml of N,N-dimethylacetamide was heated at 60° C. for 4 hours, under argon. The reaction was cooled overnight, filtered and poured into 15 ml of acetone with stirring. This solution was diluted to 100 ml with acetone. The turbid acetone layer was passed through a pad of diatomaceous earth and the pad was washed with 10 ml of water. This water was used to dissolve the viscous semi-solid which was the heptatriethylammonium derivative. A 2.6 g portion of sodium acetate was added and the solution was further diluted with 15 ml of Bio Rex ® 70 (Na+) resin and stirred for 30 minutes. This reaction was filtered into 200 ml of ethanol producing a solid. This solid was diluted with 10 ml of water and freeze-dried, giving 2.5 g of the desired heptasodium salt as a white solid, $[\alpha]_D^{26} = +24° \pm 1°$ (0.925%, water).

EXAMPLE 19

3-Trifluoromethylphenyl 2,3,6-tri-O-acetyl-4-O-(2,3,4,6-tetra-O-acetyl-α-D-glucopyranosyl)-1-thio-β-D-glucopyranoside A 2.0 g portion of 3-trifluoromethylthiophenol was reacted with 7.0 g of α-acetobromomaltose as described in Example 16, giving 3.3 g of the desired intermediate.

EXAMPLE 20

3-Trifluoromethylphenyl 4-O-(α-D-glucopyranosyl)-1-thio-β-D-glucopyranoside

A 3.5 g portion of 3-trifluoromethylphenyl 2,3,6-tri-O-acetyl-4-O-(2,3,4,6-tetra-O-acetyl-α-D-glucopyranosyl)-1-thio-β-D-glucopyranoside was reacted as described in Example 8. Rather than refrigerating overnight, this mixture was allowed to stand at room temperature for 20 hours, giving 2.5 g of the desired intermediate as a white solid, $[\alpha]_D^{26} = +25° \pm 2°$ (0.496%, methanol).

EXAMPLE 21

3-Trifluoromethylphenyl 2,3,6-tri-O-sulfo-4-O-(2,3,4,6-tetra-O-sulfo-α-D-glucopyranosyl)-1-thio-β-D-glucopyranoside heptasodium salt A 2.3 g portion of 3-trifluoromethylphenyl 4-O-(α-D-glucopyranosyl)-1-thio-β-D-glucopyranoside was reacted as described in Example 18, giving first the heptatriethylammonium and then the heptasodium derivative as 3.4 g of a white solid, $[\alpha]_D^{26} = +20° \pm 0.5°$ (1.617%, methanol).

EXAMPLE 22

3-Mercaptophenyl 2,3,6-tri-O-acetyl-4-O-(2,3,4,6-tetra-O-acetyl-α-D-glucopyranosyl)-1-thio-β-D-glucopyranoside A 1.5 g portion of 1,3-dimercaptobenzene was reacted with 7.0 g of α-acetobromomaltose as described in Example 16, giving 5.7 g of the desired intermediate as a white solid, $[\alpha]_D^{26} = +30° \pm 1°$ (0.81%, chloroform).

EXAMPLE 23

3-Mercaptophenyl 4-O-(α-D-glucopyranosyl)-1-thio-β-D-glucopyranoside

To a solution of 5.1 g of 3-mercaptophenyl 2,3,6-tri-O-acetyl-4-O-(2,3,4,6-tetra-O-acetyl-α-D-glucopyranosyl)-1-thio-β-D-glucopyranoside in 50 ml of methanol was added 0.15 g of sodium spheres. The reaction was stirred 3 hours, concentrated in vacuo and warmed with 50 ml of methanol:water (1:1). This reaction was filtered, the filtrate stirred with Dowex® 50WX8 resin and refiltered. This filtrate was concentrated in vacuo, giving 2.7 g of the desired intermediate as a yellow solid, $[\alpha]_D^{26} = +81° \pm 1°$ (0.818%, methanol).

EXAMPLE 24

3-Mercaptophenyl 2,3,6-tri-O-sulfo-4-O-(2,3,4,6-tetra-O-sulfo-α-D-glucopyranosyl)-1-thio-β-D-glucopyranoside octasodium salt A 2.5 g portion of 3-mercaptophenyl 4-O-(α-D-glucopyranosyl)-1-thio-β-D-glucopyranoside was reacted with 20.4 g of triethylamine-sulfur trioxide complex as described in Example 18, giving first the octatriethylammonium derivative and then 8.0 g of the octasodium derivative as a solid, $[\alpha]_D^{26} = +4° \pm 1°$ (1.323%, water).

EXAMPLE 25

4-Aminophenyl 2,3,6-tri-O-acetyl-4-O-(2,3,4,6-tetra-O-acetyl-α-D-glucopyranosyl)-1-thio-β-D-glucopyranoside To a slurry of 0.6 g of hexane washed 50% sodium hydride in oil in 50 ml of dimethoxyethane was added a solution of 1.7 g of 4-aminothiophenol in 25 ml of dimethoxyethane. This reaction was warmed to reflux for ½ hour under argon, then cooled to 15° C. and 8.74 g of α-acetobromomaltose was added. This reaction was heated to reflux for 7 hours, then cooled overnight and 5 ml of hexamethylphosphortriamide was added. The reaction was refluxed 4 more hours, then cooled and concentrated in vacuo. The residue was diluted with 10 ml of dimethoxyethane, then with an equal volume of water and extracted with two 50 ml portions of ether. The ether extracts were combined, extracted with 50 ml of 10% sodium carbonate solution and concentrated to a residue. This residue was purified by chromatography, giving 4.1 g of the intermediate as a yellow solid, $[\alpha]_D^{26} = +44° \pm 1°$ (1.063%, chloroform).

EXAMPLE 26

4-Aminophenyl 4-O-(α-D-glucopyranosyl)-1-thio-β-D-glucopyranoside

A 3.5 g portion of 4-aminophenyl 2,3,6-tri-O-acetyl-4-O-(2,3,4,6-tetra-O-acetyl-α-D-glucopyranosyl)-1-thio-β-D-glucopyranoside was reacted as described in Example 8, giving 1.3 g of the intermediate as a tan solid, $[\alpha]_D^{26} = +48° \pm 3°$ (0.382%, methanol).

EXAMPLE 27

4-Aminophenyl 2,3,6-tri-O-sulfo-4-O-(2,3,4,6-tetra-O-sulfo-α-D-glucopyranosyl)-1-thio-β-D-glucopyranoside heptasodium salt A solution of 1.1 g of 4-aminophenyl 4-O-(α-D-glucopyranosyl)-1-thio-β-D-glucopyranoside, 5.3 g of triethylamine-sulfur trioxide complex and 20 ml of N,N-dimethylacetamide was heated at 65°–70° C. for 6 hours, then cooled and poured into 200 ml of methyl isobutyl ketone containing 4 ml of triethylamine. The solution was decanted and the remaining syrup washed with two 25 ml portions of methyl isobutyl ketone. This solid was dissolved in 40 ml of water and poured through a column of 30 ml of Bio Rex® 70 (Na+ form) resin. The column was eluted with 250 ml of water and the eluate freeze-dried, giving a syrup which was the heptatriethylammonium derivative. This syrup was neutralized with 0.4 g of sodium acetate giving 1.1 g of the desired heptasodium derivative as an off white solid, $[\alpha]_D^{26} = +14° \pm 1°$ (1.089%, water).

EXAMPLE 28

4-(N-Acetylsulfanilamidophenyl) 2,3,6-tri-O-acetyl-4-O-(2,3,4,6-tetra-O-acetyl-α-D-glucopyranosyl)-1-thio-β-D-glucopyranoside To a solution of 1.4 g of 4-aminophenyl 2,3,6-tri-O-acetyl-4-O-(2,3,4,6-tetra-O-acetyl-α-D-glucopyranosyl)-1-thio-β-D-glucopyranoside in 15 ml of benzene:acetonitrile (1:1) was added 453 mg of N-acetylsulfanilyl chloride. The solution was allowed to stand for 3 days, then was poured into 100 ml of water and extracted with chloroform. The extract was washed with 0.5N hydrochloric acid, then saturated sodium chloride solution and evaporated to a glass. This glass was dissolved in acetone, treated with charcoal, filtered and evaporated, giving 1.67 g of the desired intermediate as a tan glass.

EXAMPLE 29

4-(Sulfanilamido)phenyl 4-O-(α-D-glucopyranosyl)-1-thio-β-D-glucopyranoside

A 1.5 g portion of 4-(N-acetylsulfanilamidophenyl) 2,3,6-tri-O-acetyl-4-O-(2,3,4,6-tetra-O-acetyl-α-D-glucopyranosyl)-1-thio-β-D-glucopyranoside was dissolved in 40 ml of ammonia saturated cold methanol and then refrigerated overnight while protected from moisture. The solution was evaporated to dryness in vacuo, extracted several times with acetonitrile and triturated with ether, giving 0.774 g of the desired intermediate as an amorphous solid.

EXAMPLE 30

4-(Sulfanilamido)phenyl 2,3,6-tri-O-sulfo-4-O-(2,3,4,6-tetra-O-sulfo-α-D-glucopyranosyl)-1-thio-β-D-glucopyranoside octasodium salt A 0.615 g portion of 4-(sulfanilamido)phenyl 4-O-(α-D-glucopyranosyl)-1-thio-β-D-glucopyranoside was reacted as described in Example 18, giving first the octatriethylammonium derivative and then 1.26 g of the octasodium derivative.

EXAMPLE 31

4-Aminophenyl 2,3,6-tri-O-acetyl-4-O-(2,3,4,6-tetra-O-acetyl-β-D-glucopyranosyl)-1-thio-β-D-glucopyranoside A 2.6 g portion of 4-aminothiophenol and 7.3 g of α-acetobromocellobiose were reacted as described in Example 16, giving 5.0 g of the desired intermediate as a white solid, mp 220°–222° C.

EXAMPLE 32

4-Aminophenyl 4-O-(β-D-glucopyranosyl)-1-thio-β-D-glucopyranoside

A 3.0 g portion of 4-aminophenyl 2,3,6-tri-O-acetyl-4-O-(2,3,4,6-tetra-O-acetyl-β-D-glucopyranosyl)-1-thio-β-D-glucopyranoside was reacted as described in Example 29, giving 1.49 g of the desired intermediate as a solid, $[\alpha]_D^{26} = -47° \pm 4°$ (0.34%, water).

EXAMPLE 33

4-Aminophenyl 2,3,6-tri-O-sulfo-4-O-(2,3,4,6-tetra-O-sulfo-β-D-glucopyranosyl)-1-thio-β-D-glucopyranoside heptasodium salt The title compound may be prepared by reacting 4-aminophenyl 4-O-(β-D-glucopyranosyl)-1-thio-β-D-glucopyranoside as described in Example 18, $[\alpha]_D^{26} = +14°$ (water).

EXAMPLE 34

4-Acetamidophenyl 4-O-(β-D-glucopyranosyl)-1-thio-β-D-glucopyranoside

To a solution of 1.36 g of 4-aminophenyl 4-O-(β-D-glucopyranosyl)-1-thio-β-D-glucopyranoside in 7 ml of water was added 0.463 g of acetic anhydride. The solution was shaken for 5 minutes then taken to dryness. The resulting glass was triturated with ethyl acetate and the solid collected, giving 1.49 g. of the desired intermediate as a white glass.

EXAMPLE 35

4-Acetamidophenyl 2,3,6-tri-O-sulfo-4-O-(2,3,4,6-tetra-O-sulfo-β-D-glucopyranosyl)-1-thio-β-D-glucopyranoside heptasodium salt A 1.4 g portion of 4-acetamidophenyl 4-O-(β-D-glucopyranosyl)-1-thio-β-D-glucopyranoside was reacted as described in Example 18, giving first the heptatriethylamine derivative and then 2.35 g of the heptasodium derivative as a white amorphous solid.

EXAMPLE 36

4-(Ethoxyoxalylamino)phenyl 2,3,6-tri-O-acetyl-4-O-(2,3,4,6-tetra-O-acetyl-α-D-glucopyranosyl)-1-thio-β-D-glucopyranoside A 10.0 g portion of 4-aminophenyl 2,3,6-tri-O-acetyl-4-O-(2,3,4,6-tetra-O-acetyl-α-D-glucopyranosyl)-1-thio-β-D-glucopyranoside was dissolved in 50 ml of diethyloxalate and refluxed for 2.5 hours. The solution was cooled, poured into one liter of ether, filtered and the filtrate poured into 2 liters of hexane. The resulting solid was collected by filtration, dissolved in ethyl acetate and evaporated to a gum which was purified by chromatography, giving 6.7 g of the desired intermediate as a yellow solid $[\alpha]_D^{26} = +31° \pm 1°$ (1.157%, chloroform).

EXAMPLE 37

4-(Ethoxyoxalylamino)phenyl 4-O-(α-D-glucopyranosyl)-1-thio-β-D-glucopyranoside

A 6.7 g portion of 4-(ethoxyoxalylamino)phenyl 2,3,6-tri-O-acetyl-4-O-(2,3,4,6-tetra-O-acetyl-α-D-glucopyranosyl)-1-thio-β-D-glucopyranoside was reacted as described in Example 29, giving 3.0 g of the desired intermediate as a white solid, $[\alpha]_D^{26} = +33° \pm 1°$ (1.11%, water).

EXAMPLE 38

4-(Ethoxyoxalylamino)phenyl 2,3,6-tri-O-sulfo-4-O-(2,3,4,6-tetra-O-sulfo-α-D-glucopyranosyl)-1-thio-β-D-glucopyranoside heptasodium salt A 2.0 g portion of 4-(ethoxyoxalylamino)phenyl 4-O-(α-D-glucopyranosyl)-1-thio-β-D-glucopyranoside was reacted as described in Example 18, giving first the heptatriethylammonium derivative and then 3.8 g of the heptasodium derivative as a tan solid, $[\alpha]_D^{26} = +19° \pm 2°$ (0.60%, water).

EXAMPLE 39

4-Acetamidophenyl 4-O-(α-D-glucopyranosyl)-1-thio-β-D-glucopyranoside

A 1.0 g portion of 4-aminophenyl 4-O-(α-D-glucopyranosyl)-1-thio-β-D-glucopyranoside was dissolved in 5 ml of water and 0.340 ml of acetic anhydride was added with vigorous stirring. After stirring 10 minutes the reaction was concentrated, reconcentrated from toluene, dissolved in ethanol and precipitated with ether, giving 836 mg of the desired intermediate.

EXAMPLE 40

4-Acetamidophenyl 2,3,6-tri-O-sulfo-4-O-(2,3,4,6-tetra-O-sulfo-α-D-glucopyranosyl)-1-thio-β-D-glucopyranoside heptasodium salt An 8.0 g portion of 4-acetamidophenyl 4-O-(α-D-glucopyranosyl)-1-thio-β-D-glucopyranoside was reacted as described in Example 18, giving first the heptatriethylammonium derivative and then 15.3 g of the heptasodium derivative.

EXAMPLE 41

Preparation of Compressed Tablet

| Ingredient | mg./Tablet |
| --- | --- |
| Active Compound | 0.5–500 |
| Dibasic Calcium Phosphate N.F. | qs |
| Starch USP | 40 |
| Modified Starch | 10 |
| Magnesium Stearate USP | 1–5 |

EXAMPLE 42

Preparation of Compressed Tablet-Sustained Action

| Ingredient | mg./Tablet |
| --- | --- |
| Active Compound as Aluminum Lake*, Micronized | 0.5–500 (as acid equivalent) |
| Dibasic Calcium Phosphate N.F. | qs |
| Alginic Acid | 20 |
| Starch USP | 35 |
| Magnesium Stearate USP | 1–10 |

*Complement modulator plus aluminum sulfate yields aluminum complement modulator. Complement modulator content in aluminum lake ranges from 5–30%.

EXAMPLE 43

Preparation of Hard Shell Capsule

| Ingredient | mg./Capsule |
| --- | --- |
| Active Compound | 0.5–500 |
| Lactose, Spray Dried | qs |
| Magnesium Stearate | 1–10 |

EXAMPLE 44

Preparation of Oral Liquid (Syrup)

| Ingredient | % W/V |
| --- | --- |
| Active Compound | 0.05–5 |
| Liquid Sugar | 75.0 |
| Methyl Paraben USP | 0.18 |
| Propyl Paraben USP | 0.02 |
| Flavoring Agent | qs |
| Purified Water qs ad | 100.0 |

EXAMPLE 45

Preparation of Oral Liquid (Elixir)

| Ingredient | % W/V |
| --- | --- |
| Active Compound | 0.05–5 |
| Alcohol USP | 12.5 |
| Glycerin USP | 45.0 |
| Syrup USP | 20.0 |
| Flavoring Agent | qs |
| Purified Water qs ad | 100.0 |

EXAMPLE 46

Preparation of Oral Suspension (Syrup)

| Ingredient | % W/V |
| --- | --- |
| Active Compound as Aluminum Lake, Micronized | 0.05–5 (acid equivalent) |
| Polysorbate 80 USP | 0.1 |
| Magnesium Aluminum Silicate, Colloidal | 0.3 |
| Flavoring Agent | qs |
| Methyl Paraben USP | 0.18 |
| Propyl Paraben USP | 0.02 |
| Liquid Sugar | 75.0 |
| Purified Water qs ad | 100.0 |

EXAMPLE 47

Preparation of Injectable Solution

| Ingredient | % W/V |
| --- | --- |
| Active Compound | 0.05–5 |
| Benzyl Alcohol N.F. | 0.9 |
| Water for Injection | 100.0 |

EXAMPLE 48

Preparation of Injectable Oil

| Ingredient | % W/V |
| --- | --- |
| Active Compound | 0.05–5 |
| Benzyl Alcohol | 1.5 |
| Sesame Oil qs ad | 100.0 |

EXAMPLE 49

Preparation of Intra-Articular Product

| Ingredient | Amount |
| --- | --- |
| Active Compound | 2–20 mg. |
| NaCl (physiological saline) | 0.9% |
| Benzyl Alcohol | 0.9% |
| Sodium Carboxymethylcellulose | 1–5% |
| pH adjusted to 5.0–7.5 | |
| Water for Injection qs ad | 100% |

EXAMPLE 50

Preparation of Injectable Depo Suspension

| Ingredient | % W/V |
| --- | --- |
| Active Compound | 0.05–5 (acid equivalent) |
| Polysorbate 80 USP | 0.2 |
| Polyethylene Glycol 4000 USP | 3.0 |
| Sodium Chloride USP | 0.8 |
| Benzyl Alcohol N.F. | 0.9 |
| HCl to pH 6–8 | qs |
| Water for Injection qs ad | 100.0 |

EXAMPLE 51

Preparation of Dental Paste

| Ingredient | % W/V |
| --- | --- |
| Active Compound | 0.05–5 |
| Zinc Oxide | 15 |
| Polyethylene Glycol 4000 USP | 50 |
| Distilled Water qs | 100 |

EXAMPLE 52

Preparation of Dental Ointment

| Ingredient | % W/W |
| --- | --- |
| Active Compound | 0.05–5 |
| Petrolatum, White USP qs | 100 |

EXAMPLE 53

Preparation of Dental Cream

| Ingredient | % W/W |
| --- | --- |
| Active Compound | 0.05–5 |
| Mineral Oil | 50 |
| Beeswax | 15 |
| Sorbitan Monostearate | 2 |
| Polyoxyethylene 20 Sorbitan Monostearate | 3 |
| Methyl Paraben USP | 0.18 |
| Propyl Paraben USP | 0.02 |
| Distilled Water qs | 100 |

EXAMPLE 54

Preparation of Topical Cream

| Ingredient | % W/W |
| --- | --- |
| Active Compound | 0.05–5 |
| Sodium Lauryl Sulfate | 1 |
| Propylene Glycol | 12 |
| Stearyl Alcohol | 25 |
| Petrolatum, White USP | 25 |
| Methyl Paraben USP | 0.18 |
| Propyl Paraben USP | 0.02 |
| Purified Water qs | 100 |

EXAMPLE 55

Preparation of Topical Ointment

| Ingredient | % W/W |
| --- | --- |
| Active Compound | 0.05–5 |
| Cholesterol | 3 |
| Stearyl Alcohol | 3 |
| White Wax | 8 |
| Petrolatum, White USP qs | 100 |

EXAMPLE 56

Preparation of Spray Lotion (Non-aerosol)

| Ingredient | % W/W |
| --- | --- |
| Active Compound | 0.05–5 |
| Isopropyl Myristate | 20 |
| Alcohol (Denatured) qs | 100 |

EXAMPLE 57

Preparation of Buccal Tablet

| Ingredient | mq./Tablet |
| --- | --- |
| Active Ingredient | 3.25 |
| 6 x Sugar | 290.60 |
| Acacia | 14.53 |
| Soluble Starch | 14.53 |
| F. D. & C. Yellow No. 6 Dye | 0.49 |
| Magnesium Stearate | 1.60 |
| | 325.00 |

The final tablet will weigh about 325 mg. and may be compressed into buccal tablets in flat faced or any other tooling shape convenient for buccal administration.

EXAMPLE 58

Preparation of Lozenge

| Ingredient | g./Lozenge |
| --- | --- |
| Active Ingredient | 0.0140 |
| Kompact ® Sugar, (Sucrest Co.) | 0.7138 |
| 6 x Sugar | 0.4802 |
| Sorbitol (USP Crystalline) | 0.1038 |
| Flavor | 0.0840 |
| Magnesium Stearate | 0.0021 |
| Dye | qs |
| Stearic Acid | 0.0021 |
| | 1.4000 |

The ingredients are compressed into ⅞" flat based lozenge tooling. Other shapes may also be utilized.

The compounds of the present invention may be administered internally, e.g., orally, intra-articularly or parenterally, to a warm-blooded animal to inhibit complement in the body fluid of the animal, such inhibition being useful in the amelioration or prevention of those reactions dependent upon the function of complement, such as inflammatory process and cell membrane damage induced by antigen-antibody complexes. A range of doses may be employed depending on the mode of administration, the condition being treated and the particular compound being used. For example, for intravenous or subcutaneous use from about 5 to about 50 mg/kg/day, or every six hours for more rapidly excreted salts, may be used. For intra-articular use for large joints such as the knee, from about 2 to about 20 mg/joint/week may be used, with proportionally smaller doses for smaller joints. The dosage range is to be adjusted to provide optimum therapeutic response in the warm-blooded animal being treated. In general, the amount of compound administered can vary over a wide range to provide from about 5 mg/kg to about 100 mg/kg of body weight of animal per day. The usual daily dosage for a 70 kg subject may vary from about 350 mg to about 3.5 g. Unit doses of the acid or salt can contain from about 0.5 mg to about 500 mg.

The compounds of the present invention may also be administered topically in the form of ointments, creams, lotions and the like, suitable for the treatment of complement dependent dermatological disorders.

Moreover, the compounds of the present invention may be administered in the form of dental pastes, ointments, buccal tablets and other compositions suitable for application periodontally for the treatment of periodontitis and related diseases of the oral cavity.

In therapeutic use, the compounds of this invention may be administered in the form of conventional pharmaceutical compositions. Such compositions may be formulated so as to be suitable for oral or parenteral administration. The active ingredient may be combined in admixture with a pharmaceutically acceptable carrier, which carrier may take a wide variety of forms depending on the form of preparation desired for administration, i.e., oral or parenteral. The compounds can be used in compositions such as tablets. Here, the principal active ingredient is mixed with conventional tabletting ingredients such as corn starch, lactose, sucrose, sorbitol, talc, stearic acid, magnesium stearate, dicalcium phosphate, gums, or similar materials as nontoxic pharmaceutically acceptable diluents or carriers. The tablets or pills of the novel compositions can be laminated or otherwise compounded to provide a dosage form affording the advantage of prolonged or delayed action of predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate and the like. A particularly advantageous enteric coating comprises a styrene maleic acid copolymer together with known materials contributing to the enteric properties of the coating. The tablet or pill may be colored through the use of an appropriate non-toxic dye, so as to provide a pleasing appearance.

The liquid forms in which the novel compositions of the present invention may be incorporated for administration include suitable flavored emulsions with edible oils, such as, cottonseed oil, sesame oil, coconut oil, peanut oil, and the like, as well as elixirs and similar pharmaceutical vehicles. Sterile suspensions or solutions can be prepared for parenteral use. Isotonic preparations containing suitable preservatives are also desirable for injection use.

The term "dosage form", as described herein, refers to physically discrete units suitable as unitary dosage for warm-blooded animal subjects, each unit containing a predetermined quantity of active component calculated to produce the desired therapeutic effect in association with the required pharmaceutical diluent, carrier or vehicle. The specification for the novel dosage forms of this invention are indicated by characteristics of the active component and the particular therapeutic effect to be achieved or the limitations inherent in the art of compounding such an active component for therapeutic use in warm-blooded animals as disclosed in this specification. Examples of suitable oral dosage forms in accord with this invention are tablets, capsules, pills, powder packets, granules, wafers, cachets, teaspoonfuls, dropperfuls, ampules, vials, segregated multiples of any of the foregoing and other forms as herein described.

The complement modulating activity of compounds of this invention has been demonstrated by one or more of the following identified tests: (i) Test Code 026 (C1inhibitor): This test measures the ability of activated human C1 to destroy fluid phase human C2 in the presence of C4 and appropriate dilutions of the test compound. An active inhibitor protects C2 from C1 and C4; (ii) Test Code 035 (C3–C9 inhibitor): This test determines the ability of the late components of human complement (C3–C9) to lyse EAC 142 in the presence of appropriate dilutions of the test compound. An active inhibitor protects EAC 142 from lysis by human C3–C9; (iii) Cap 50 Test: Here, appropriate amounts of the test compound are added to a pool of guinea pig or human serum in vitro, after which the undiluted serum capillary tube assay of U.S. Pat. No. 3,876,376 is run. The concentration of compound inhibiting 50% is reported; and (iv) Guinea Pig Intraperitoneal Test (GPIP): Guinea pigs weighing about 300 g are dosed intraperitoneally (i.p.) with 200 mg/kg of the test compound dissolved in saline and adjusted to pH 7–8. Approximately 0.4 ml blood samples, taken by orbital sinus puncture 2 hours and 6 hours after injections, are collected directly into centifuge tubes; 5 ml blood samples, taken by decapitation 24 hours after injection, are collected directly into beakers. The samples are allowed to clot, centrifuged, and the resultant sera are assayed for complement activity using the capillary complement assay. Percent inhibition is calculated by comparison with simultaneous controls. The results of the GPIP appear in Table I together with results of Test Code 026, 035, and Cap 50. Table I shows that the principal compounds of the invention possess highly significant complement modulating activity in warm-blooded animals.

TABLE I

| | Biological Activities | | | In vivo Activity Guinea Pig % Inhibition | | |
|---|---|---|---|---|---|---|
| | In vitro Activity | | | Intraperitoneal Time (hours) | | |
| | C1 026* | C-Late 035* | Guinea Pig | 2 | 6 | 24 |
| Compound | Wells | Wells | Cap 50* | | | |
| 2,5-bis(sulfooxy)phenyl 2, 3, 6-tri-O-sulfo-4-O-(2,3,4,6-tetra-O-sulfo-α-D-glucopyranosyl)-1-thio-β-D-glucopyranoside nonasodium salt | 9** | 2 | 151 | 83 | 77 | — |
| 4-(sulfanilamido)phenyl 2,3,6-tri-O-sulfo-4-O-(2,3,4,6-tetra-O-sulfo-α-D glucopyranosyl)-1-thio-β-D-glucopyranoside octasodium salt | 5 | | >500 | | | |
| 2,5-bis(sulfooxy)phenyl 2,3,6-tri-O-sulfo-4-O-(2,3,4,6-tetra-O-sulfo-α-D-glucopyranosyl)-1-sulfinyl-β-D-glucopyranoside nonasodium salt | 11 | 2 | | | | |
| 4-methoxyphenyl 2,3,6-tri-O-sulfo-4-O-(2,3,4,6-tetra-O-sulfo-α-D-glucopyranosyl)-1-thio-β-D-glucopyranoside heptasodium salt | 4 | | 336 | | | |
| 4-aminophenyl 2,3,6-tri-O-sulfo- | 9 | | 419 | 61 | 19 | 42 |

TABLE I-continued

Biological Activities

| Compound | In vitro Activity | | | In vivo Activity Guinea Pig % Inhibition Intraperitoneal Time (hours) | | |
|---|---|---|---|---|---|---|
| | Cl 026* Wells | C-Late 035* Wells | Guinea Pig Cap 50* | 2 | 6 | 24 |
| 4-O-(2,3,4,6-tetra-O-sulfo-α-D-glucopyranosyl)-1-thio-β-D-glucopyranoside heptasodium salt | | | | | | |
| 4-(sulfooxy)phenyl 2,3,6-tri-O-sulfo-4-O-(2,3,4,6-tetra-O-sulfo-α-D-glucopyranosyl)-1-thio-β-D-glucopyranoside octasodium salt | 8 | | 366 | | | |
| 2-carboxyphenyl 2,3,6-tri-O-sulfo-4-O-(2,3,4,6-tetra-O-sulfo-α-D-glucopyranosyl)-1-thio-β-D-glucopyranoside octasodium salt | 8 | | 463 | | | |
| 4-fluorophenyl 2,3,6-tri-O-sulfo-4-O-(2,3,4,6-tetra-O-sulfo-α-D-glucopyranosyl -D-glucopyranoside heptasodium salt | 8 | | >500 | | | |
| 3-trifluoromethylphenyl 2,3,6-tri-O-sulfo-4-O-(2,3,4,6-tetra-O-sulfo-α-D-glucopyranosol)-1-thio-β-D-glucopyranoside heptasodium salt | 5 | | 320 | | | |
| 4-(ethoxyoxalylamino)phenyl 2,3,6-tri-O-sulfo-4-O-(2,3,4,6-tetra-O-sulfo-α-D-glucopyranosyl)-1-thio-β-D-glucopyranoside heptasodium salt | 8 | | | 81 | 71 | 32 |
| 3-mercaptophenyl 2,3,6-tri-O-sulfo-4-O-(2,3,4,6-tetra-O-sulfo-α-D-glucopyranosyl)-1-thio-β-D-glucopyranoside octasodium salt | 11 | 3 | | | | |
| 4-acetamidophenyl 2,3,6-tri-O-sulfo-4-O-(2,3,4,6-tetra-O-sulfo-β-D-glucopyranosyl)-1-thio-β-D-glucopyranoside heptasodium salt | 6 | | | | | |
| 4-acetamidophenyl 2,3,6-tri-O-sulfo-4-O-(2,3,4,6-tetra-O-sulfo-β-D-glucopyranosyl)-1-thio-β-D-glucopyranoside heptasodium salt | 7 | | | 86 | 66 | 15 |

*Tests identified by code hearin. For a discussion of the tests, see "Systematic Discovery & Evaluation of Complement Inhibitors," N. Bauman et al., Immunopharmacology 3: 317–24 (1981).
**Activity in wells, a serial dilution assay; higher well number indicates higher activity. The serial dilutions are two-fold.

We claim:
1. A compound selected from those of the formula:

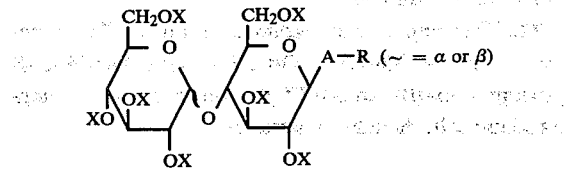

wherein X is —$SO_3M$ and M is a nontoxic pharmaceutically acceptable cation salt, wherein the salt forming moiety is selected from the group consisting of alkali metal, alkaline earth metal, aluminum, ammonia, zinc and substituted ammonia selected from the group consisting of trialkylamine ($C_1$–$C_6$), piperidine, pyrazine, alkanolamine ($C_2$–$C_6$) and cycloalkylamine ($C_3$–$C_6$); A is selected from the group consisting of —S— and —SO—; and R is phenyl mono-, di- or trisubstituted with a moiety selected from the group consisting of hydrogen, OX, alkoxy ($C_1$–$C_3$), hydroxy, halo, trifluoromethyl, amino, mercapto, acetylamino, —COOM, —$NHCOCOOC_2H_5$ and

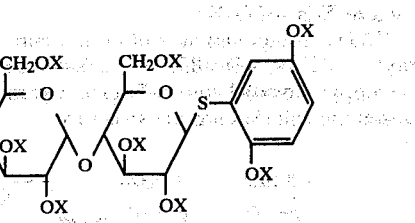

2. The compound according to claim 1, 2,5-bis(sulfooxy)phenyl 2,3,6,-tri-O-sulfo-4-O-(2,3,4,6-tetra-O-sulfo-α-D-glucopyranosyl)-1-thio-β-D-glucopyranoside nonasodium salt having the structure where X is —$SO_3Na$.

3. The compound according to claim 1, 2,5-bis(sulfooxy)phenyl 2,3,6-tri-O-sulfo-4-O-(2,3,4,6-tetra-O-α-D-glucopyranosyl)-1-thio-β-D-glucopyranoside nonatriethylammonium salt having the structure

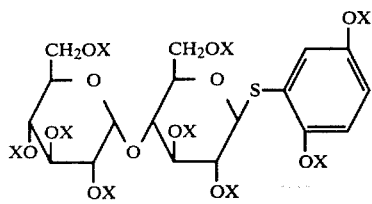

where X is $SO_3^- NH^+(C_2H_5)_3$.

4. The compound according to claim 1, 4-(sulfanilamido)phenyl 2,3,6-tri-O-sulfo-4-O-(2,3,4,6-tetra-O-sulfo-α-D-glucopyranosyl)-1-thio-β-D-glucopyranoside octasodium salt, having the structure

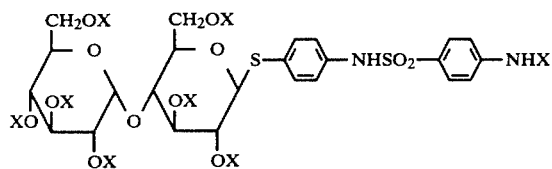

where X is $-SO_3Na$.

5. The compound according to claim 1, 2,5-bis-(sulfooxy)phenyl 2,3,6-tri-O-sulfo-4-O-(2,3,4,6-tetra-O-sulfo-α-D-glucopyranosyl)-1-sulfinyl-β-D-glucopyranoside nonasodium salt, having the structure

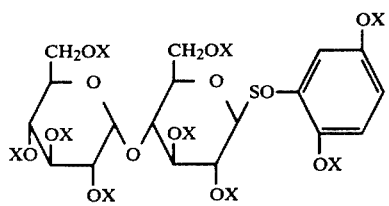

where X is $-SO_3Na$.

6. The compound according to claim 1, 4-methoxyphenyl 2,3,6-tri-O-sulfo-4-O-(2,3,4,6-tetra-O-sulfo-α-D-glucopyranosyl)-1-thio-β-D-glucopyranoside heptasodium salt having the structure

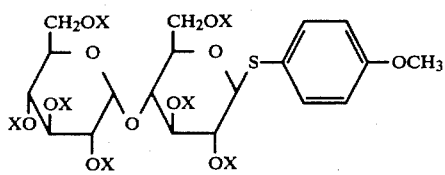

where X is $-SO_3Na$.

7. The compound according to claim 1, 4-aminophenyl 2,3,6-tri-O-sulfo-4-O-(2,3,4,6-tetra-O-sulfo-α-D-glucopyranosyl)-1-thio-β-D-glucopyranoside heptasodium salt, having the structure

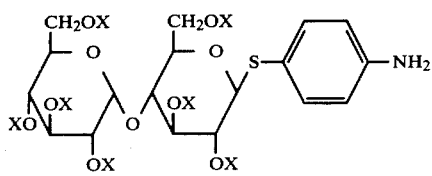

where X is $-SO_3Na$.

8. The compound according to claim 1, 4-aminophenyl 2,3,6-tri-O-sulfo-4-O-(2,3,4,6-tetra-O-sulfo-β-D-glucopyranosyl)-1-thio-β-D-glucopyranoside heptasodium salt, having the structure

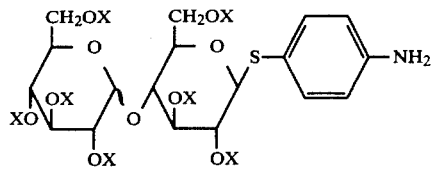

where X is $-SO_3Na$.

9. The compound according to claim 1, 4-(sulfooxy)phenyl 2,3,6-tri-O-sulfo-4-O-(2,3,4,6-tetra-O-sulfo-α-D-glucopyranosyl)-1-thio-β-D-glucopyranoside octasodium salt having the structure

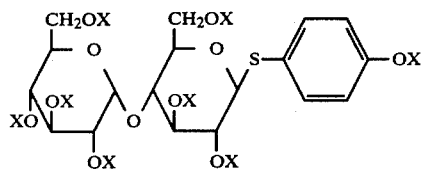

where X is $-SO_3Na$.

10. The compound according to claim 1, 2-carboxyphenyl 2,3,6-tri-O-sulfo-4-O-(2,3,4,6-tetra-O-sulfo-α-D-glucopyranosyl)-1-thio-β-D-glucopyranoside octasodium salt, having the structure

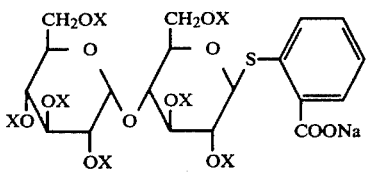

where X is $-SO_3Na$.

11. The compound according to claim 1, 4-fluorophenyl 2,3,6-tri-O-sulfo-4-O-(2,3,4,6-tetra-O-sulfo-α-D-glucopyranosyl)-1-thio-β-D-glucopyranoside heptasodium salt, having the structure

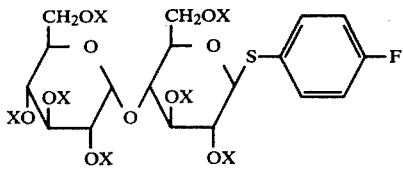

where X is $-SO_3Na$.

12. The compound according to claim 1, 3-trifluoromethylphenyl 2,3,6-tri-O-sulfo-4-O-(2,3,4,6-tetra-O-sulfo-α-D-glucopyranosyl)-1-thio-β-D-glucopyranoside heptasodium salt, having the structure

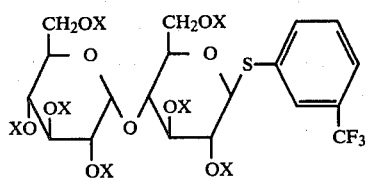

where X is —SO₃Na.

13. The compound according to claim 1, 4-(ethoxyoxalylamino)phenyl 2,3,6-tri-O-sulfo-4-O-(2,3,4,6-tetra-O-sulfo-α-D-glucopyranosyl)-1-thio-β-D-glucopyranoside heptasodium salt, having the structure

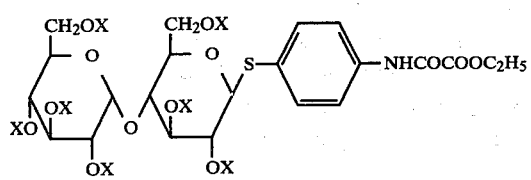

where X is —SO₃Na.

14. The compound according to claim 1, 3-mercaptophenyl 2,3,6-tri-O-sulfo-4-O-(2,3,4,6-tetra-O-sulfo-α-D-glucopyranosyl)-1-thio-β-D-glucopyranoside octasodium salt, having the structure

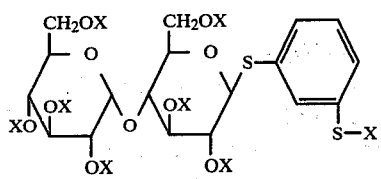

where X is —SO₃Na.

15. The compound according to claim 1, 4-acetamidophenyl 2,3,6-tri-O-sulfo-4-O-(2,3,4,6-tetra-O-sulfo-β-D-glucopyranosyl)-1-thio-β-D-glucopyranoside heptasodium salt, having the structure

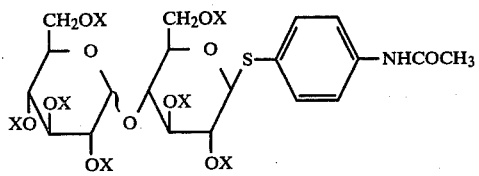

where X is —SO₃Na.

16. The compound according to claim 1, 4-acetamidophenyl 2,3,6-tri-O-sulfo-4-O-(2,3,4,6-tetra-O-sulfo-α-D-glucopyranosyl)-1-thio-β-D-glucopyranoside heptasodium salt, having the structure

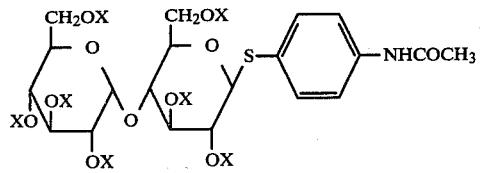

where X is —SO₃Na.

17. A compound selected from those of the formula:

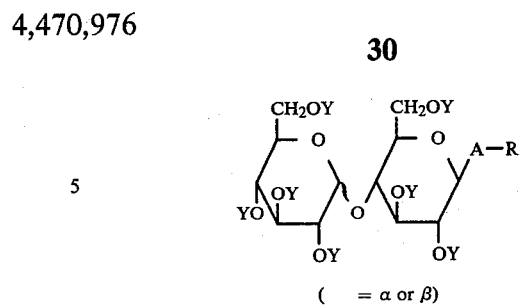

( ⁓ = α or β)

wherein Y is selected from the group consisting of hydrogen and —COCH₃; A is selected from the group consisting of —S— and —SO—; and R is phenyl mono-, di- or trisubstituted with a moiety selected from the group consisting of hydrogen, alkoxy (C₁–C₃), hydroxy, halo, trifluoromethyl, amino, mercapto, acetylamino, COOH, —NHCOCOOC₂H₅ and

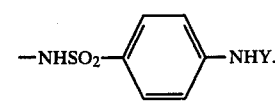

18. The compound according to claim 17, 2,5-dihydroxyphenyl 4-O-(α-D-glucopyranosyl)-1-thio-β-D-glucopyranoside, having the structure

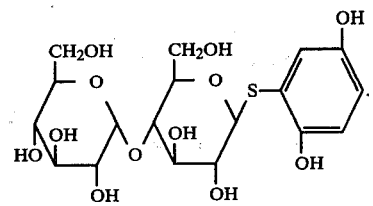

19. A method of modulating the complement system in a warm-blooded animal which comprises administering to said warm-blooded animal an effective complement modulating amount of a pharmaceutically acceptable compound selected from those of the formula:

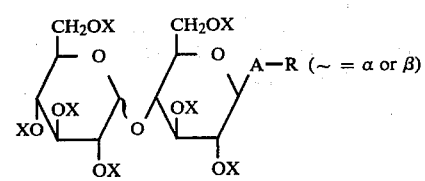

wherein X is —SO₃M and M is a nontoxic pharmaceutically acceptable cation salt, wherein the salt forming moiety is selected from the group consisting of alkali metal, alkaline earth metal, aluminum, ammonia, zinc and substituted ammonia selected from the group consisting of trialkylamine (C₁–C₆), piperidine, pyrazine, alkanolamine (C₂–C₆) and cycloalkylamine (C₃–C₆); A is selected from the group consisting of —S— and —SO—; and R is phenyl mono-, di- or trisubstituted with a moiety selected from the group consisting of hydrogen, OX, alkoxy (C₁–C₃), hydroxy, halo, trifluoromethyl, amino, mercapto, acetylamino, —COOM, —NHCOCOOC₂H₅ and

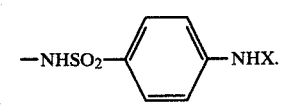

* * * * *